United States Patent [19]
Garlick et al.

[11] Patent Number: 5,329,817
[45] Date of Patent: Jul. 19, 1994

[54] ULTRASONIC HOLOGRAPHY IMAGING METHOD AND APPARATUS

[75] Inventors: George F. Garlick; Glen C. Dunham, both of Kennewick, Wash.

[73] Assignee: Advanced Imaging Systems, Richland, Wash.

[21] Appl. No.: 796,711

[22] Filed: Nov. 22, 1991

[51] Int. Cl.$^5$ ............................................. G01N 29/06
[52] U.S. Cl. ....................................... 73/605; 73/603; 367/9; 367/10
[58] Field of Search ................. 367/9, 10; 73/603, 605

[56] References Cited

U.S. PATENT DOCUMENTS

| | | | |
|---|---|---|---|
| 3,585,847 | 6/1971 | Brenden | 73/605 |
| 3,832,888 | 9/1974 | Langlois | 73/605 |
| 4,028,934 | 6/1977 | Sollish | 73/603 |
| 4,393,712 | 7/1983 | Sandhu | 73/603 |

Primary Examiner—Hezron E. Williams
Assistant Examiner—Rose M. Finley
Attorney, Agent, or Firm—Wells, St. John, Roberts, Gregory & Matkin

[57] ABSTRACT

A preferred embodiment of this invention is illustrated in FIG. 4 showing an offset and tilted object transducer 50 being rotated about a system axis 51 to sequentially insonify the object from various acute incident angles $\theta$ to the system axis to provide images of the out-of-focus structures at spaced locations at the hologram detection surface 18 at different spaced times. If the pulse rate of the object transducer is greater than the fusion of the eye, the eye is able to average two or more images into a single perceived image. Likewise, video equipment that receives images at a rate greater than 30 Hertz will average two or more images and display the image at a rate of approximately 30 Hertz. Additionally, external video processing may be utilized to electronically average two or more images electronically to obtain an averaged image at any time constant desired by the operator. Such a system effectively neutralizes or blends the out-of-focus structure of an object spaced from a selected focus plane 27 while maintaining the structure within the plane in sharp consistent contrast to provide consistent, quality images of the internal structure of an object 12.

30 Claims, 9 Drawing Sheets

ULTRASONIC HOLOGRAPHY IMAGING METHOD AND APPARATUS

TECHNICAL FIELD

This invention relates to ultrasonic holographic imaging processes and apparatus and more particularly to such processes and apparatus for imaging internal structure in a selected focal plane of an article and to minimize image distortions caused by article structures spaced from the selected focal plane or "out-of-focus" structures.

BACKGROUND OF THE INVENTION

Although commercial application of ultrasonic holography has been actively pursued by many persons in the scientific and industrial communities for many years, only limited results have been obtained even though it was once thought that ultrasonic holography held great promise. It was felt that the application of ultrasonic holography was particularly applicable to the fields of non-destructive testing of materials and medical diagnostics of soft tissues that are relatively transparent or translucent to ultrasonic radiation. One of the principal problems that has been encountered and not effectively resolved is the difficulty of obtaining consistent, high quality images. Solutions have been particularly elusive in obtaining undistorted, high quality images of selected focused structures in an object under investigation because of the interference or shadowing of other out-of-focus structures in an object. A typical prior art ultrasonic holographic imaging system for inspecting a selected plane in an object is illustrated in FIG. 1.

Figure 1:
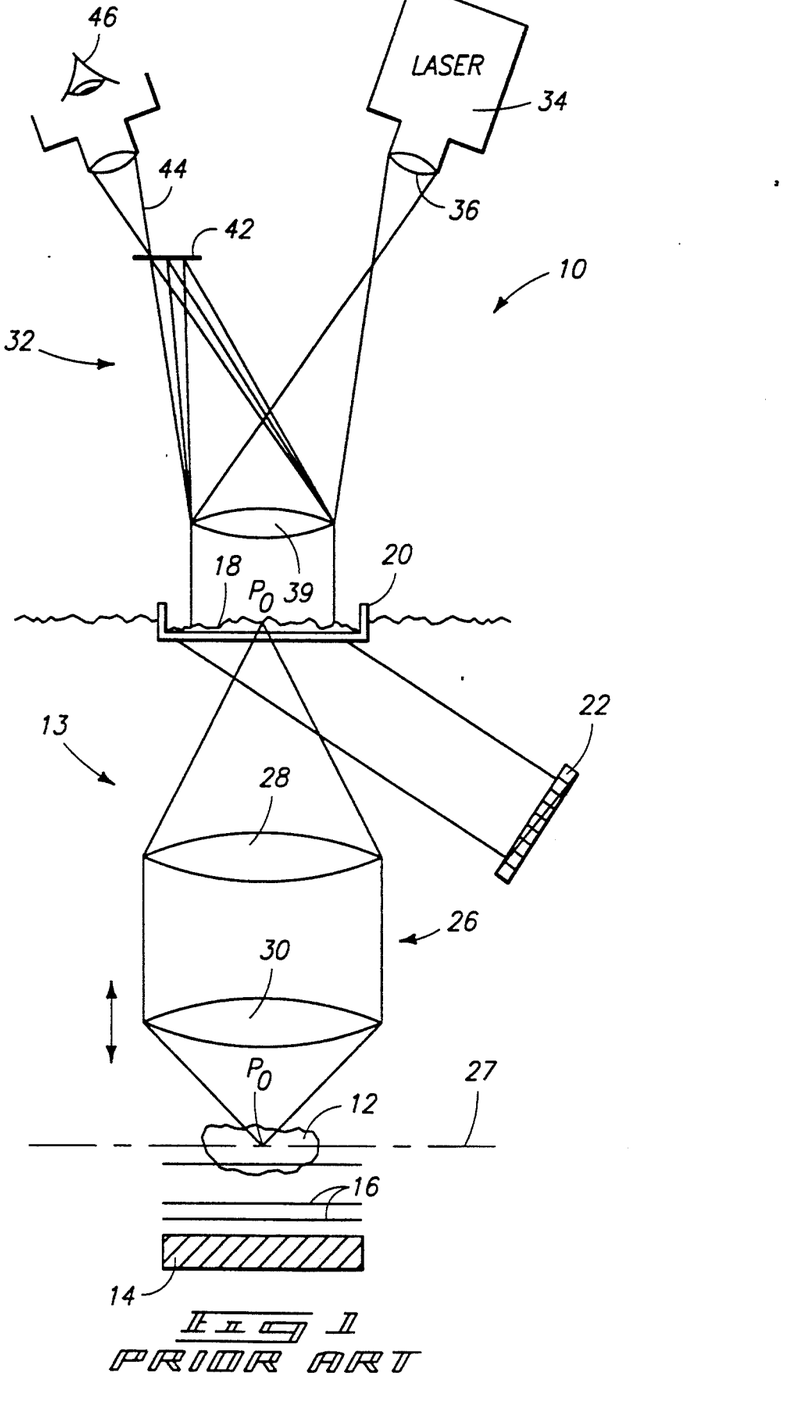
FIG. 1 is a schematic view of a prior art ultrasonic holographic imaging system for imaging article structures in a selected image plane on a detector surface and generating a visual image of the article structure.

Such a typical "real time" ultrasonic holographic imaging system is identified in FIG. 1 with numeral 10. The system 10 is intended to inspect the interior of an object 12. The system 10 generally has a hologram generating sub-system 13 and a hologram viewing sub-system (optical sub-system) 32. Principal components are ultrasonic transducers, generally referred to as an object transducer 14 for generating ultrasonic plane waves 16 to insonify the object 12 and a reference transducer 22 for generating an off-axis beam.

The ultrasonic energy transmitted through the object 12 is directed through a liquid medium to a hologram detection surface 18, which is generally an area of a liquid-gas interface or liquid surface, such as a water surface. Generally the hologram detection surface 18 is physically isolated in a detection container 20 to minimize distortions caused by vibration. The ultrasonic reference transducer 22 generates an off-axis ultrasonic beam that is also directed to the hologram detection surface 18 to form a standing wave hologram. It is frequently desirable to pulse the transducers 14 and 22 at desired intervals to minimize dynamic distortions of the detector surface 18.

Generally an ultrasonic lens assembly 26 is utilized to provide a focused hologram of a desired plane 27 within the object 12. In the example shown, the assembly 26 has a stationary lens 28 having a focal length coincident with the plane of the hologram detection surface 18. A movable complementary lens 30 is provided to be moved to focus on the selected object plane 27 of the object 12 to inspect an internal structures $P_0$ that is within the selected object plane 27.

The optical subsystem 32 includes a source of coherent light, preferably a laser 34 for generating a beam of coherent light. The laser light beam is directed through a laser lens 36 to achieve a point source that is located at or near the focal point of a collimating lens 38 and then onto the hologram detector surface to illuminate the hologram. The diffracted coherent light radiation containing holographic information is directed back through the optical lens 38 and separated into precisely defined diffracted orders in the focal plane of the collimating lens 38. A filter 42 is used to block all but a first order pattern 44 for "real time" observation by a human eye 46 or an optical recorder, such as a video camera.

Figure 2:
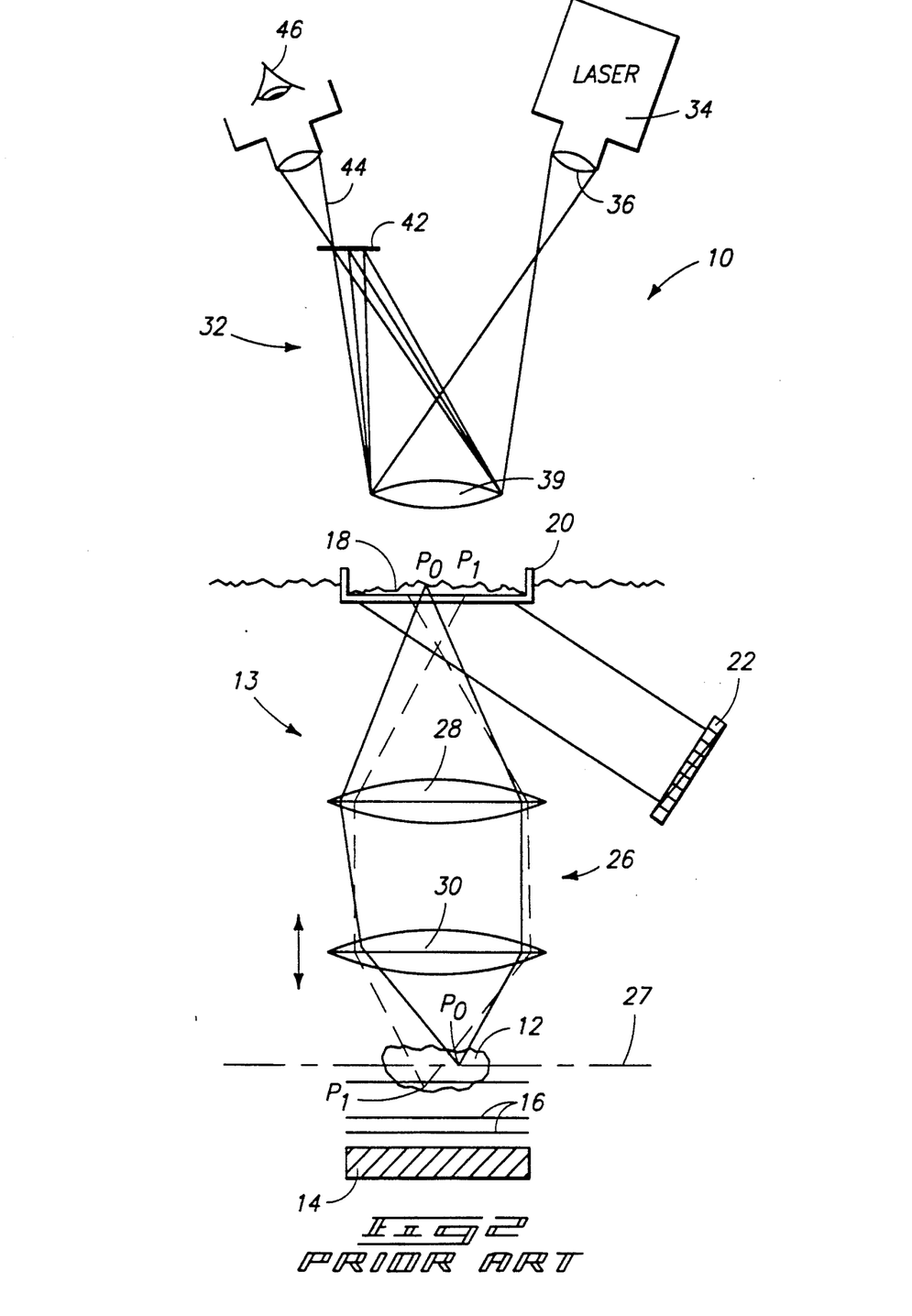
FIG. 2 is a schematic view similar to FIG. 1 except showing the imposition of an interfering, out-of-focus structure spaced from the selected image plane.
Figure 3:
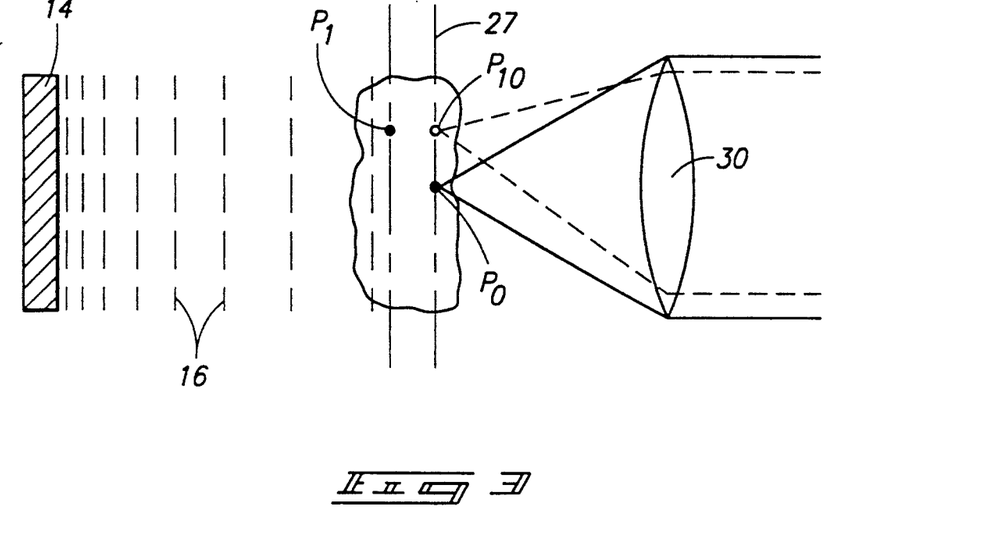
FIG. 3 is a fragmentary detailed schematic view of a portion of the prior art system illustrated in FIG. 2 illustrating in further detail the imposition of an out-of-focus article structure into the selected image plane.

FIGS. 2 and 3 illustrate graphically the problem encountered by distortions or image degradation caused by object structures $P_1$ that are spaced from the focused object plane 27. Such speed object structures are referred to as "out-of-focus" structures, and are identified generally as $P_1$. The out-of-focus structure $P_1$, when insonified, retransmits spherical waves and a shadow that is transferred by the optical system 26 to a holographic pattern $P_1$ in the detection surface as illustrated in FIG. 2. FIG. 3 illustrates the phenomenon in more detail in which the out-of-focus structure $P_1$ forms a shadow identified as $P_{10}$ in the plane 27. The shadow $P_{10}$ is in effect imaged on the detector surface of the hologram 18.

One of the principal objects of this invention is to minimize and neutralize those out-of-focus structures of the object such as $P_1$ to provide a more consistent, high quality image structure in the selected focal plane 27 of the object. A further object is to minimize the distortion caused by such out-of-focus structures utilizing rather inexpensive techniques and apparatus.

These and other objects and advantages of this invention will become apparent upon reading the following detailed description of the preferred and alternate embodiments of this invention.

BRIEF DESCRIPTION OF THE DRAWINGS

Preferred embodiments of the invention are described below with reference to the accompanying drawings, which are briefly described below.

FIG. 14 is a simplified schematic view of an alternate embodiment using an array of object transducers directed to insonify the object at the plurality of acute incident angles.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 4:
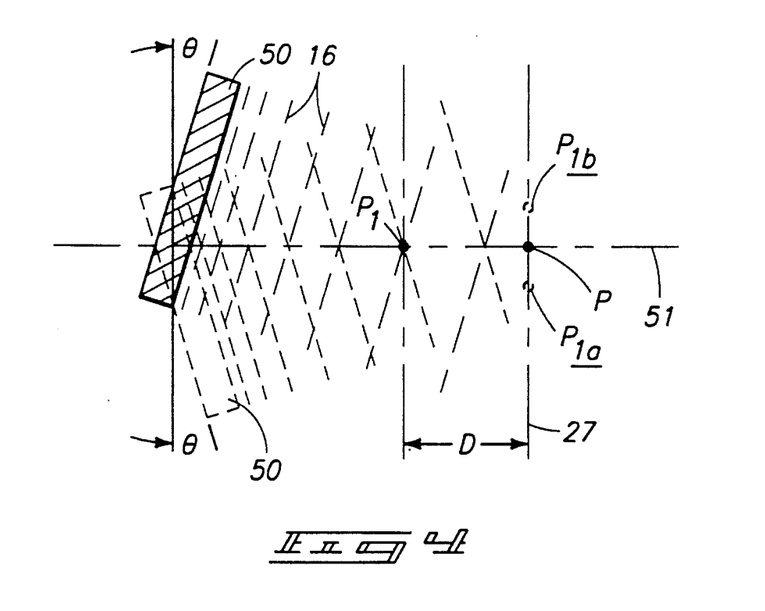
FIG. 4 is a fragmentary detailed schematic view of a portion of a preferred embodiment of this invention illustrating the insonification of the object at multiple acute angles to an system axis, in which an object transducer is shown inclined and off-set relative to the system axis, both in solid line and dotted line.

FIGS. 4, 5, 7 and 15 illustrate a preferred embodiment of ultrasonic holographic imaging apparatus of the present invention. Specifically, FIG. 4 illustrates an object transducer 50 that is mounted at an inclined angle with respect to the system axis 51 in which a center axis of the transducer 52 intersects the central axis 51 at an angle $\theta$ (FIG. 5) so that the object beam from the transducer 50 is directed at the object at an acute intersecting incident angle. The incident angle is preferably less than 10°. Optimally the incident angle should be between 5°–10°. The object transducer 50 is moved to alternate inclined positions angularly spaced from each other about the system axis 51 to direct an object beam at a plurality of acute incident angles through the object. More specifically, in FIG. 4, the object transducer 50, shown in solid line, directs plane waves 16 through the object so that the out-of-focus structure $P_1$ is imposed into the focal plane 27 as a phantom or shadow structure $P_{1a}$. The object transducer 50 is then sequentially moved to a plurality of other positions about the axis 51 to insonify the object at a plurality of acute incident angles $\theta$. One of the alternate positions of the object transducer is illustrated in dotted line in FIG. 4 for insonifying the object at a different acute incident angle $\theta$ to project a shadow of structure $P_1$ into the focal plane 27 as a phantom structure $P_{1b}$. Consequently, the object transducer 50 is rotated at the incline angle $\theta$ about the axis 51 to sequentially position the object transducer at a plurality of angularly spaced positions to direct time-spaced object beams through the object at the various acute incident angles $\theta$ to generate shadow or phantom structures $P_1$ in the focal plane 27. This system is shown in additional detail in FIG. 5.

Figure 5:
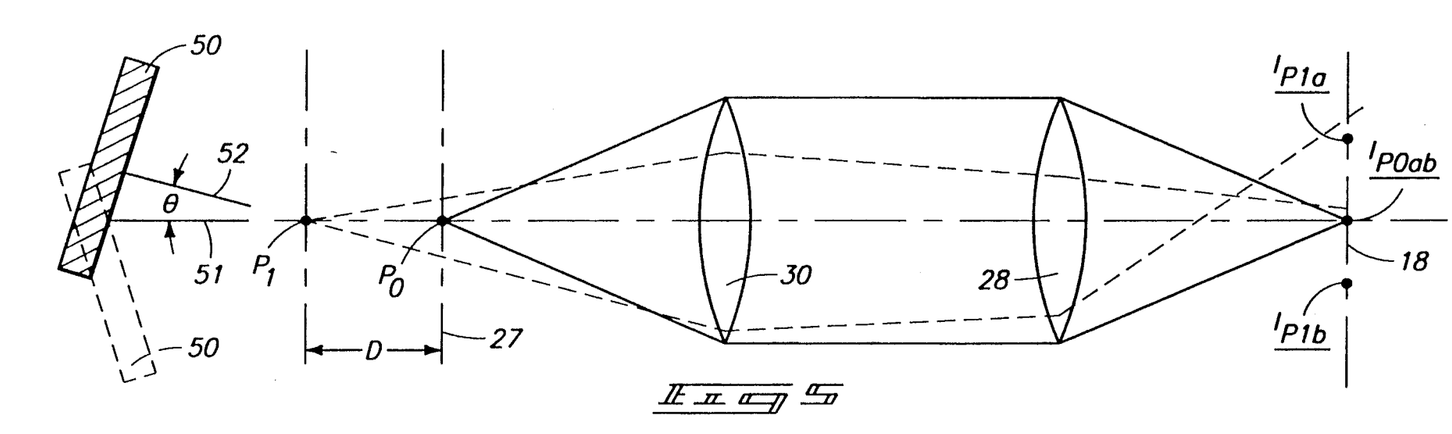
FIG. 5 is a fragmentary detailed schematic view similar to FIG. 4 except illustrating imaging the out-of-focus structure at spaced locations on the detection surface when insonifying the object at the multiple acute angles.

FIG. 5 illustrates the imaging of the selected focal plane 27 onto the hologram detection surface 18 in which the structure $P_O$ has a projected image $I_{POab}$ in the detection plane indicating that the structure $P_O$ remains at a constant position at the detection surface independently of the angular position of the object transducer 50 about the system center line 51. However, when the object transducer 50 is in the position shown in solid line, the out-of-focus structure $P_1$ forms an image at the detection surface identified as $I_{P1a}$. The image of the out-of-focus structure $P_1$ when viewed by the transducer 50 in the position illustrated in the dotted line is at a spaced location identified as $I_{P1b}$. Consequently for each angular position of the transducer, the structural elements in the focal plane 27 remain at the same positions in the detection surface 18, however the out-of-focus structure $P_1$ changes to a different position at each different position of the object transducer 50. Thus, each different position of the object transducer produces a out-of-focus structural image $P_1$ at a different spaced location on the detection surface 18.

Figure 6:
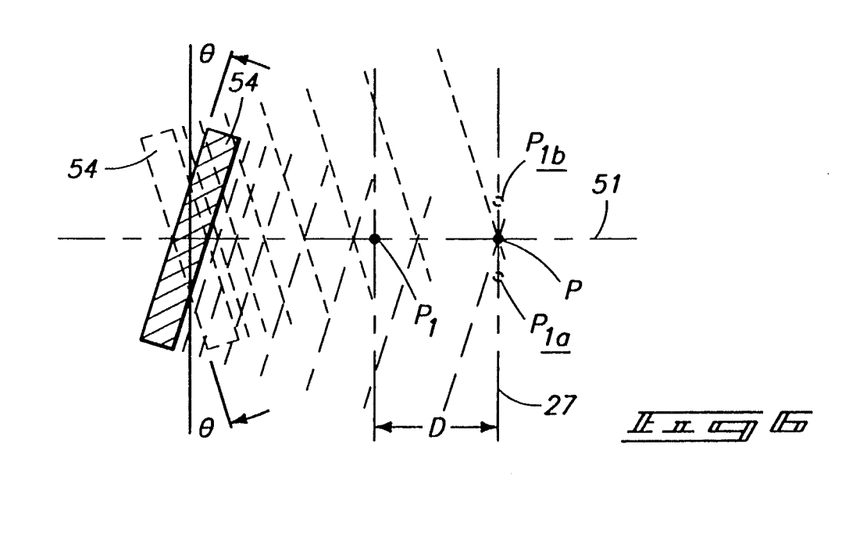
FIG. 6 is a fragmentary detailed schematic view similar to FIG. 4 except showing a portion of an alternate embodiment, in which the object transducer is shown inclined but centered relative to the system axis, in both the solid line and dotted line.

FIG. 6 illustrates an object transducer 54 that is centered on the center axis 51 and not laterally offset like the object transducer 50 in FIGS. 4 and 5. In FIG. 6, the transducer 54 is merely rotated to the plurality of different angular positions about the axis 51 to provide the plurality of time sequenced object beams for sequentially insonifying the object to produce phantom images $P_{1a}$ and $P_{1b}$ in the selected focal plane 27. It should be noted that each of the structures $P_O$ within the plane 27 appears to be stationary on the detector surface 18 while the structure $P_1$ appears to move and change positions at each of the plurality of positions of the rotated transducer 54. The object transducer 50 is inclined at angle $\theta$ with respect to a normal plane of the central or system axis 51.

It is desirable to pulse the object transducers 50, 54 at frequencies between approximately 25 Hertz and 180 Hertz. It is further desirable to move the transducers between each pulse so that the distance between each image of the out-of-focus structure $I_{P1a}$ and $I_{P1b}$, etc., on the detection surface is spaced at distances greater than one-fourth of the wave length of the object beam, but less than 10 wave lengths. It is preferable that the spacing between the sequentially derived images of the out-of-focus structure in the detector surface be approximately 3 to 4 wave lengths.

Figure 7:
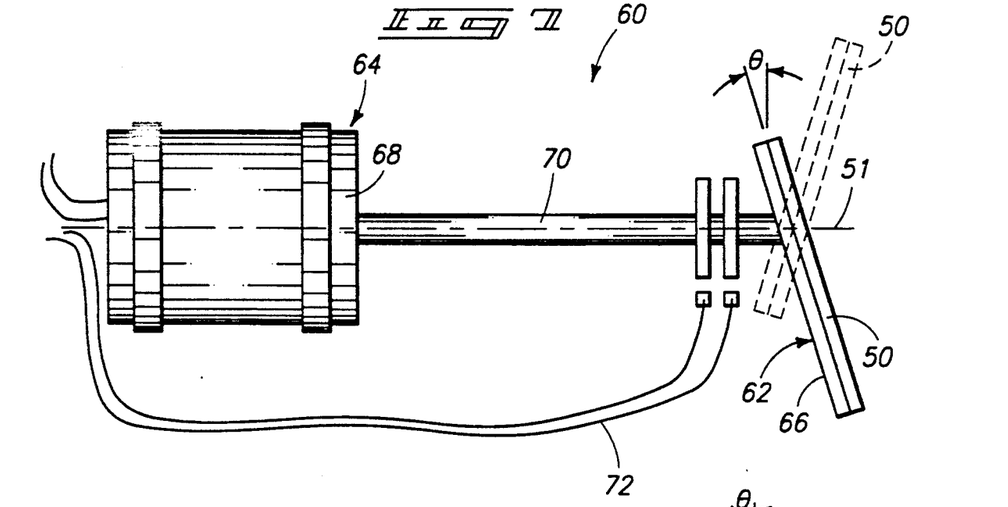
FIG. 7 is an isolated side elevational view of a drive for rotating the object transducer illustrated in FIGS. 4 and 5.

FIG. 7 illustrates a part of an ultrasonic transducer means generally designated with the numeral 60. The ultrasonic transducer means 60 includes a transducer support means 62 for supporting the object transducer 50 at the inclined angle $\theta$ and laterally offset from the system axis 51. The ultrasonic transducer means 60 includes a rotating means generally designated with the numeral 64 that includes a support plate 66 on which the transducer 50 is mounted. The support plate is mounted on a shaft 70 that is rotated by a motor 68. An actuation or pulse signal applying means 72 is connected through the shaft to the transducer for pulsing the transducer at the desired pulse rate or frequency as the transducer 54 is rotated about the system axis through the plurality of angularly spaced locations to insonify the object at a multitude of inclined incident angles to produce out-of-focus structural images at correspondingly different locations on the detection surface.

Figure 8:
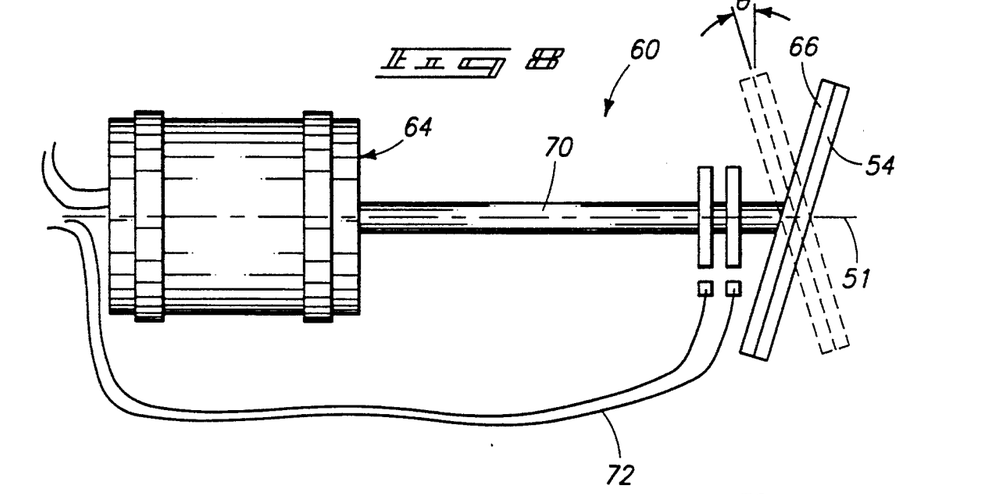
FIG. 8 is an isolated side elevational view of a drive for rotating the object transducer illustrated in FIG. 6.

FIG. 8 is similar to FIG. 7 except that the supporting plate 66 and the object transducer 54 are centrally mounted with respect to the system axis 51 at the inclined angle $\theta$ for rotation about the axis 51 sequentially through the plurality of angularly spaced positions to insonify the object at the different incident angles.

Figure 9:
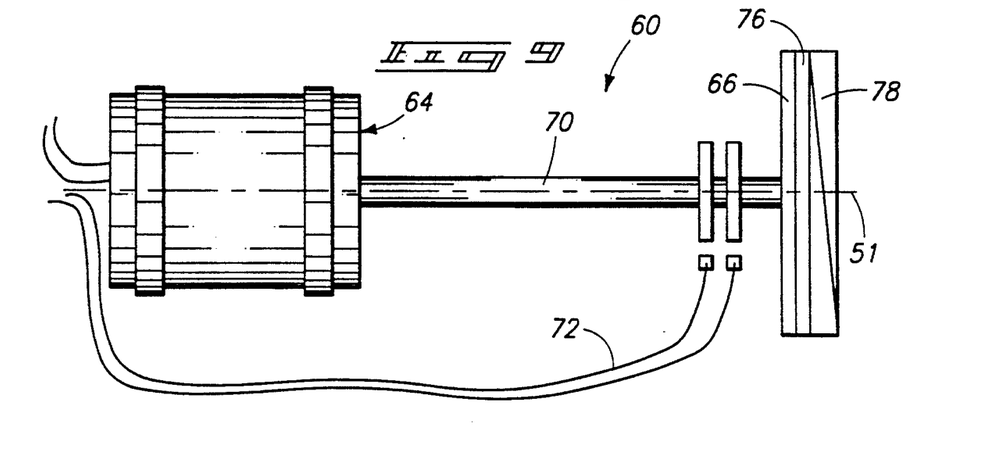
FIG. 9 is an isolated side elevational view of a drive for rotating the object transducer having a double refractory disc mounted thereon for redirecting the object beam at the acute incident angles to the system axis.

FIG. 9 represents an alternative embodiment in which the support plates 66 and a object transducer 76 are mounted in planes normal to the system axis 51. Such a system includes a double-wedged disk 78 that includes two wedged disks that are secured together and placed on the front face of the transducer 76 to generate object beams at different acute angles of inclination to the object as the shaft 70 is rotated.

Figure 11:
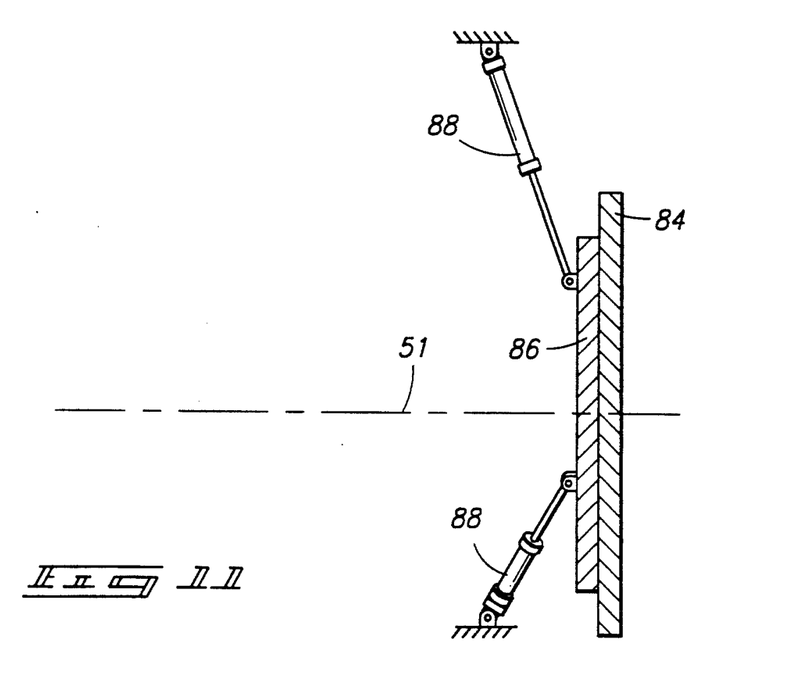
FIG. 11 is an isolated side elevational view of the alternate mechanism illustrated in FIG. 10.
Figure 12:
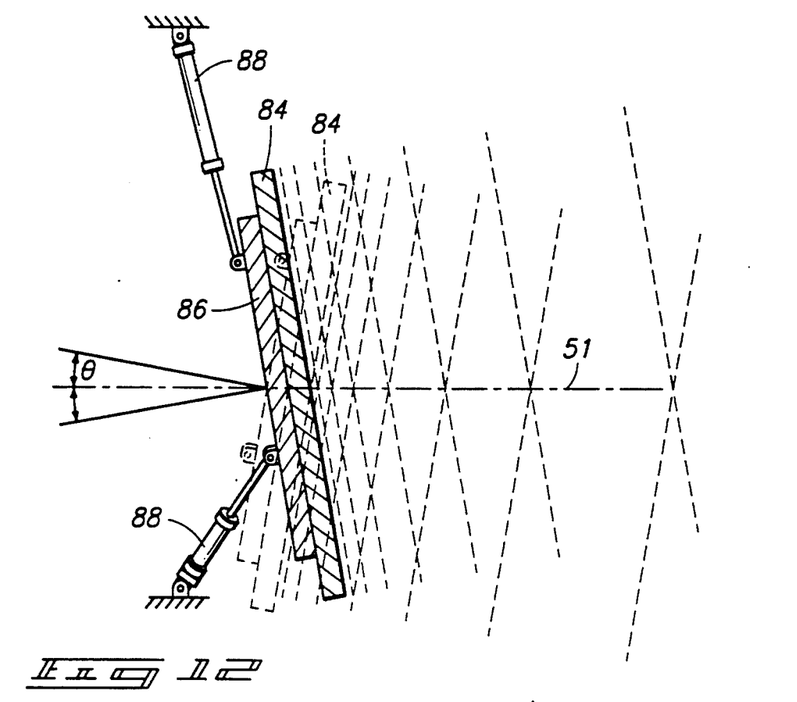
FIG. 12 is an isolated side elevational view similar to FIG. 11 showing the object transducer being tilted about the system axis in two positions, one being in solid line and the other in dotted line.
Figure 13:
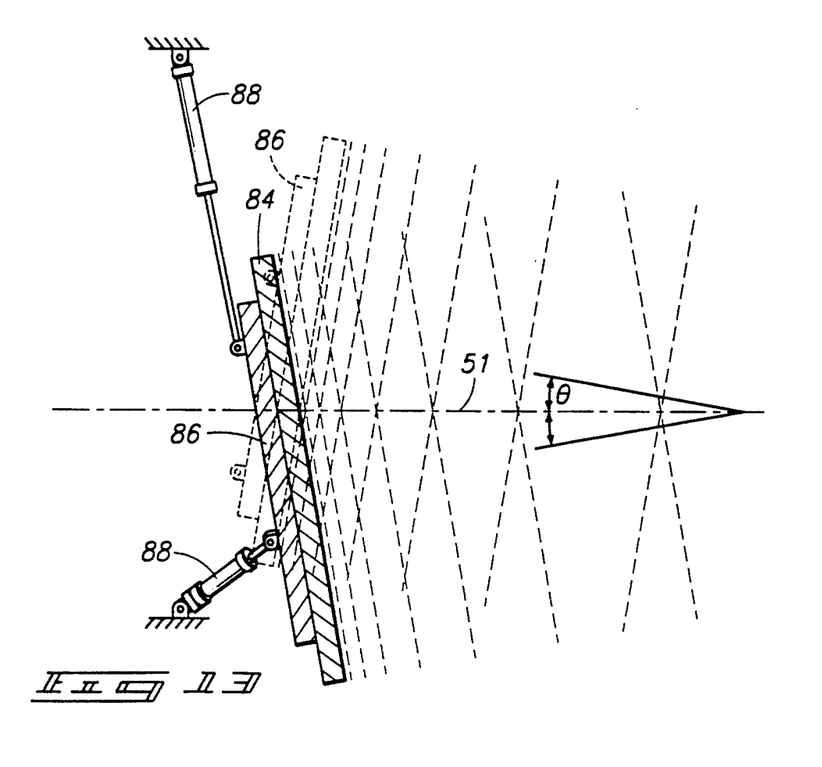
FIG. 13 is an isolated side elevational view similar to FIG. 12 except showing the object transducer being tilted and moved radially outward of the system axis in two positions, one being in solid line and the other in dotted line.

FIGS. 10-13 illustrate a further embodiment in which an object transducer 84 is mounted to a support plate 86 that is in turn movably supported by actuators 88. The actuators 88 are, in a preferred configuration, hydraulic or air pistons that are individually actuated to move the transducer to desired locations with respect to the system axis 51. The actuators are individually controlled by a position control circuit generally designated with the numeral 90 to progressively move the object transducer 84 sequentially to the various positions for directing the object beam through the object at the various different angular positions. For example in FIG. 12, the actuators 88 are sequentially actuated to sequentially tilt the object transducer 84 about the system axis 51 with the transducer 87 being centered with respect to the central axis 51. Consequently rather than rotating the object transducer 84, it is tilted to the various positions by the actuators 88. FIG. 13 illustrates a different operation of the actuators in which the transducer 84 is laterally moved or offset from the central axis 51 and tilted to generate the desired spaced object beams for insonifying the object at the various angularly spaced positions about the system axis 51.

FIG. 14 shows a further alternate embodiment utilizing an array 100 of transducers that are stationarily mounted at angularly spaced positions about the system axis 51. In FIG. 14, three transducers 100a, 100b and 100c are illustrated. The array 100 is controlled by an electronic circuit that includes a pulse circuit 102 for generating pulses at defined frequencies between 24 Hertz and 180 Hertz. The pulse circuit is connected to amplification circuit 104 to amplify the generated pulses. A switching circuit 106 sequentially activates the array 100 of transducers to generate the time spaced object beams at the desired angularly spaced acute incident angles.

Figure 10:
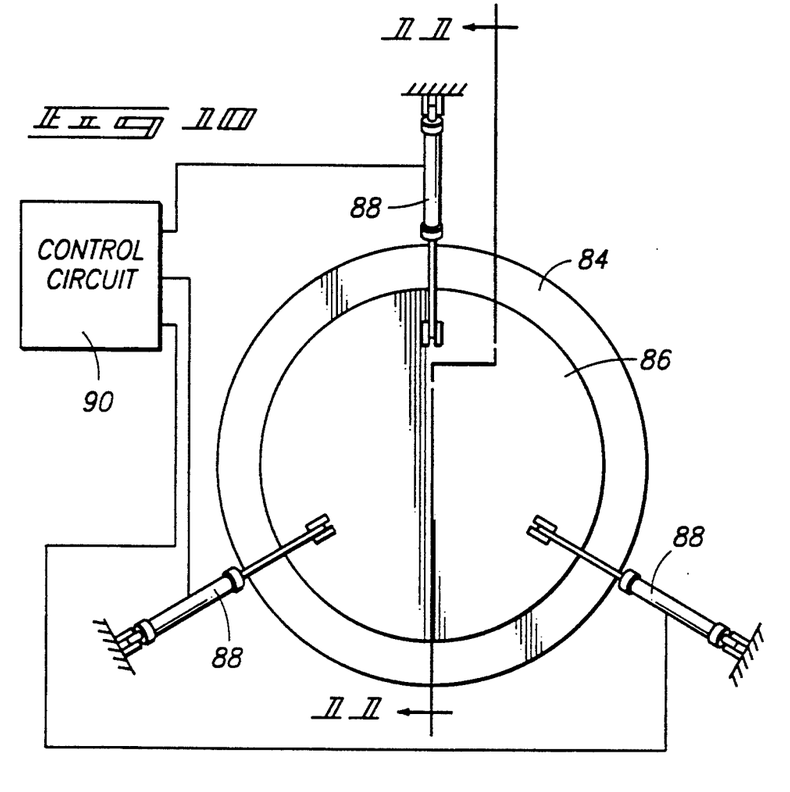
FIG. 10 is an isolated rear elevational view of an alternate object transducer moving mechanism for moving the object transducer to a plurality of positions to generate object beams at the plurality of acute incident angles.

In summary, FIGS. 4-7 show a rotating technique, and FIGS. 10-12 show a tilting technique for moving a single transducer to the various desired angularly spaced positions. FIG. 14 shows an array of stationary transducers at the various positions that are sequentially activated for generating the time spaced object beams. FIG. 9 shows a modification of the rotating technique utilizing a double wedge refractory disk for generating the acute incident angles of object radiation.

Figure 15:
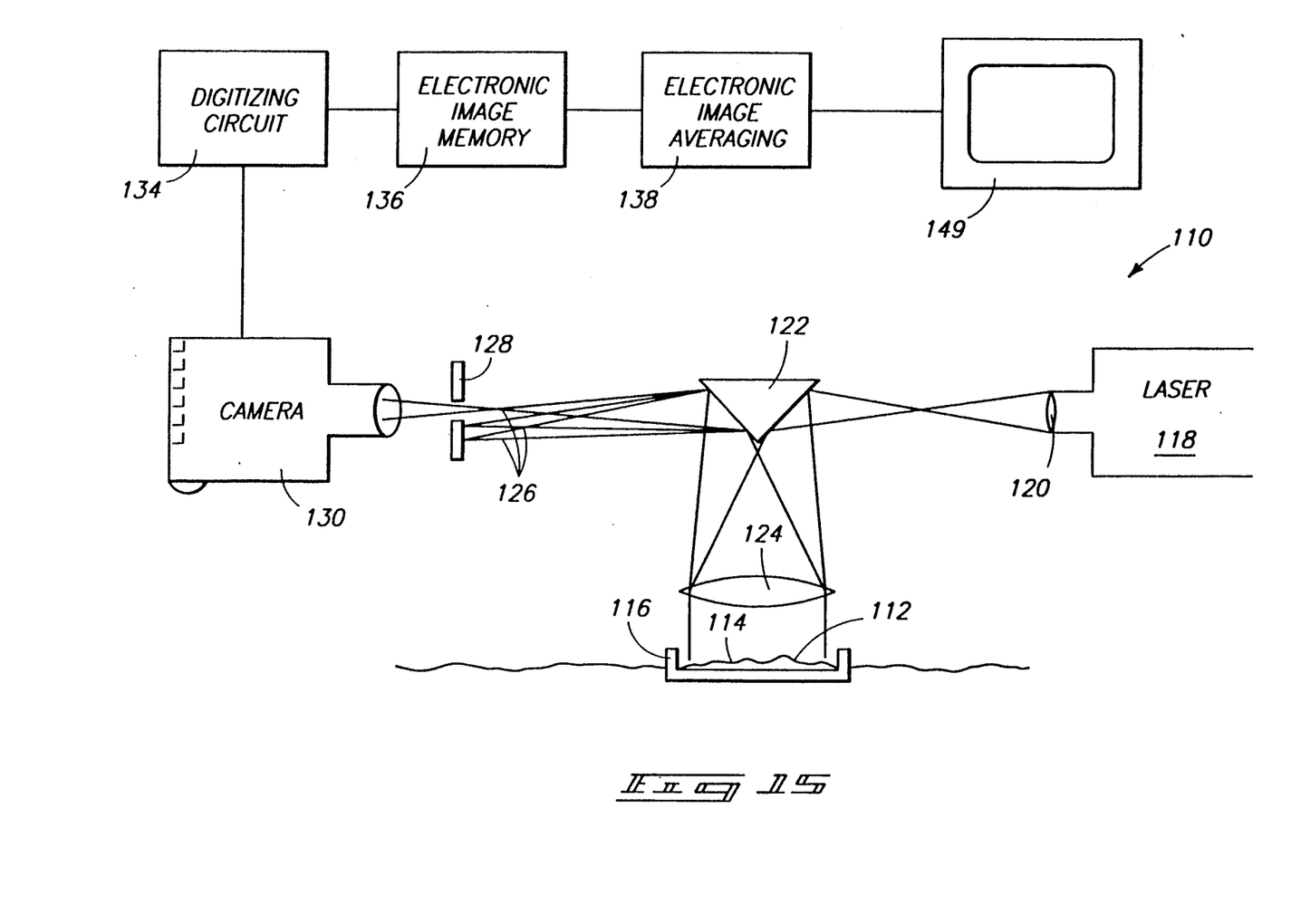
FIG. 15 is a combination schematic and electric block diagram of an optical reconstruction system of a preferred embodiment to average and neutralize out-of-focus structure in a sequence of holographic images.

FIG. 15 illustrates an optical hologram reconstruction system 110 that is utilized in conjunction with the hologram detection surface 112, preferably a liquid surface, that forms ultrasonic hologram 114. Preferably, the hologram detection surface 112 is isolated in a mini-tank 116 similar to mini-tank 20 illustrated in FIGS. 1 and 2.

A coherent light source 118, such as laser, generates a coherent light beam 119 that is directed through a focusing lens 120 onto a mirror 122 and through a collimating lens 124 illuminating the hologram detection surface 112 with visible coherent light. The coherent light illuminating the hologram 114 is diffracted in a number of diffraction order beams 126. The beams are directed to a spacial filter 128 that filters out all but a first order (positive or negative or both) diffracted beam which is again diffracted from the mirror 122 to a video camera 130.

Preferably, the optical hologram reconstruction system 110 includes a digitizing circuit 134 connected to the video camera 130 for digitizing the pixel signals from the camera 130. The digitized signals of each image is stored in a frame image memory 136. Preferably, the image memory 136 contains sufficient digitized information constituting a number of image frames. An electronic image averaging circuit means 138 receives the image information from the memory 136 to average the signals over a number of frames. Preferably, more than three frames are averaged so as to neutralize or minimize the values of the out-of-focus structural elements appearing in the images.

Since the out-of-focus structural features are located at different locations in the different images, the averaging effectively neutralizes the out-of-focus structure into the image background. The averaged, resulting image then is displayed on a visual display unit 149 such as a CRT tube or a television set. Because of the electronic averaging of the digitized image signals, the reconstruction system 110 is not dependent upon the pulse rate of the object transducers. The averaging of the image frames from the video camera can be averaged over any time constant as desired by the operator.

Alternatively, the human eye may be utilized as the averaging system because of the fusion rate of the eye being approximately 24 Hertz. Consequently if the images are presented to the eye at rates greater than 24 Hertz, the eye will naturally average the images and thus neutralize the out-of-focus objects presented in the image. For example, two images presented at a 40 Hertz rate are integrated into a single perceived image by the eye. Consequently, the out-of-focus portion of the image either appears as part of the background or appears to represent fuzzy representations whereas the structural elements in the selected object plane 27 will appear clear and sharp.

A third technique for averaging the sequentially generated images of the hologram relates to the frame rate of the video equipment used to display the image. Since the rate is generally 30 Hertz, a pulse rate greater than 30 Hertz will cause the video equipment to automatically average two or more images. Preferably, the object transducer pulse rate or image generation rate is between 24 Hertz and 180 Hertz. If the system is operated at a rate greater than 180 Hertz, it may be detrimental to the generation of a consistent, quality hologram because of the recovery rate of the liquid surface of the detector surface 112 between pulses.

Consequently by utilizing a rather simple technique to insonify the object sequentially from a plurality of acute incident angles, the out-of-focus structure $P_1$ that is spaced from the selected focus plane 27 may be removed or minimized in distorting the final image that is displayed.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An ultrasonic holographic imaging apparatus for generating a holographic image of object structure in a selected plane of an object that is place in the path of ultrasound while minimizing holographic image distortions caused by interfering structure of the object spaced from the selected object plane defining an out-of-focus structure, comprising:
    a) an ultrasonic holographic detection surface aligned with an optical axis;
    b) an ultrasonic transducer means for (1) directing a coherent object beam of ultrasound along the optical axis and through the object to the ultrasonic holographic detection surface, and (2) directing a coherent ultrasonic reference beam to the holographic detection surface to interfere with the object beam to form an ultrasonic hologram at the detection surface;
    c) an ultrasonic imaging lens system aligned with and extending along the optical axis between the object and the holographic detection surface for focusing ultrasound from the selected object plane onto the holographic detection surface; and
    d) wherein the ultrasonic transducer means directs the ultrasonic object beam through the object at a plurality of acute incident angles relative to the optical axis to project images of the out-of-focus structure on the detection surface at spaced locations corresponding to the acute incident angles.

2. The ultrasonic holographic imaging apparatus as defined in claim 1 wherein the plurality of acute incident angles are angularly spaced about the optical axis to position the image of the out-of-focus structure on the detection surface at corresponding angularly spaced locations about the optical axis.

3. The ultrasonic holographic imaging apparatus as defined in claim 1 wherein the acute incident angles are each less than 10 degrees.

4. The ultrasonic holographic imaging apparatus as defined in claim 1 wherein the ultrasonic transducer means sequentially directs the object beam through the object at the plurality of acute incident angles to sequentially project the out-of-focus structure on the detection surface at the spaced locations.

5. The ultrasonic holographic imaging apparatus as defined in claim 4 wherein the ultrasonic transducer means includes (1) a plane wave object transducer, and (2) an object transducer moving means for sequentially moving the object transducer relative to the optical axis to sequentially insonify the object, including the out-of-focus structure, at the plurality of acute incident angles.

6. The ultrasonic holographic imaging apparatus as defined in claim 5 wherein the object transducer is mounted at an incline relative to the optical axis and wherein the object transducer moving means rotates the inclined object transducer about the optical axis sequentially through the plurality of acute incident angles.

7. The ultrasonic holographic imaging apparatus as defined in claim 6 wherein the object transducer is centered on the optical axis.

8. The ultrasonic holographic imaging apparatus as defined in claim 6 wherein the object transducer is centered spaced from the optical axis.

9. The ultrasonic holographic imaging apparatus as defined in claim 5 wherein the object transducer is mounted for selective tilting movement relative to the optical axis and wherein the object transducer moving means sequentially tilts the object transducer to the plurality of acute angles.

10. The ultrasonic holographic imaging apparatus as defined in claim 9 wherein the object transducer is centered on the optical axis.

11. The ultrasonic holographic imaging apparatus as defined in claim 9 wherein the object transducer moving means sequentially moves the object transducer radially outward from the optical axis and tilts the object transducer to the plurality of acute angles.

12. The ultrasonic holographic imaging apparatus as defined in claim 4 wherein the ultrasonic transducer means includes (1) a plane wave object transducer centered on the optical axis for generating the object beam, and (2) a double wedge refractory element intermediate the object transducer and the object for receiving the object beam and redirecting the object beam at one of the acute angles to the optical axis, and (3) rotating means for rotating the refractory element about the optical axis to the plurality of acute angles.

13. The ultrasonic holographic imaging apparatus as defined in claim 12 wherein the double wedge refractory element is mounted to the object transducer and wherein the rotating means rotates the object transducer and refractory element together.

14. The ultrasonic holographic imaging apparatus as defined in claim 1 wherein the ultrasonic transducer means comprises an array of object transducers for insonifying the object at the plurality of acute incident angles.

15. The ultrasonic holographic imaging apparatus as defined in claim 14 wherein the ultrasonic transducer means includes activation means for sequentially activating the object transducers for sequentially directing the object beam through the object at the plurality of acute incident angles to sequentially project the out-of-focus structure onto the detection surface at the spaced locations.

16. The ultrasonic holographic imaging apparatus as defined in claim 4 wherein the ultrasonic transducer means pulses the object beam at a pulse rate of 180 Hz. or less.

17. The ultrasonic holographic imaging apparatus as defined in claim 16 wherein the ultrasonic transducer means pulses the object beam at a pulse rate of approximately 30 Hz.

18. The ultrasonic holographic imaging apparatus as defined in claim 16 wherein the ultrasonic transducer means pulses the object beam at a pulse rate of approximately 120 Hz.

19. The ultrasonic holographic imaging apparatus as defined in claim 1 wherein the plurality of acute incident angles are spaced sufficiently from the optical axis to space the locations of the imaged out-of-focus structure on the detection surface at distances between one-fourth and 10 times the wave length of the object beam.

20. The ultrasonic holographic imaging apparatus as defined in claim 19 wherein the spaced locations are separated at a distance of approximately 3-4 times the wave length of the object beam.

21. The ultrasonic holographic imaging apparatus as defined in claim 1 wherein the acute incident angles are between 5 and 10 degrees inclusive.

22. The ultrasonic holographic imaging apparatus as defined in claim 1 wherein the apparatus further comprises (1) optical hologram reconstruction means focused on the detection surface for generating a sequence of optical images of the selected object in which the out-of-focus structure is located at different locations in the images, (2) optical-to-electronic conversion means converting the optical images to a sequence of digitized electronic images, and (3) electronic signal averaging means for averaging the electronic signals of the sequence of digitized electronic images to neutralize those signals corresponding to the out-of-focus structure.

23. The ultrasonic holographic imaging apparatus as defined in claim 1 wherein the apparatus further comprises (1) optical hologram reconstruction means focused on the detection surface for generating a sequence of optical images of the selected object in which the out-of-focus structure is located at different locations in the images, and (2) averaging means for averaging the sequence of images to neutralize the out-of-focus structure relative to the structure in the selected plane.

24. An ultrasonic holographic imaging process for generating a holographic image of object structure in a selected plane of an object that is place in the path of ultrasound while minimizing holographic image distortions caused by interfering structure of the object spaced from the selected object plane defining an out-of-focus structure, comprising the steps of:
 a) aligning an ultrasonic holographic detection surface with a system axis;
 b) directing a coherent object beam of ultrasound along the system axis and through the object to the ultrasonic holographic detection surface;
 c) directing a coherent ultrasonic reference beam to the holographic detection surface to interfere with the object beam to form an ultrasonic hologram at the detection surface;
 d) aligning an ultrasonic imaging lens system along the system axis between the object and the holographic detection surface for focusing ultrasound from the selected object plane onto the holographic detection surface; and
 e) directing the ultrasonic object beam through the object at a plurality of acute incident angles relative to the system axis to project images of the out-of-focus structure on the detection surface at spaced locations corresponding to the acute incident angles.

25. The ultrasonic holographic imaging process as defined in claim 24 further comprising the step of spacing the acute incident angles angularly about the system axis to position the image of the out-of-focus structure on the detection surface at corresponding angularly spaced locations about the system axis.

26. The ultrasonic holographic imaging process as defined in claim 24 wherein the acute incident angles are between 5 and 10 degrees.

27. The ultrasonic holographic imaging process as defined in claim 24 wherein the object beam is sequentially directed through the object at the plurality of acute incident angles to sequentially project the out-of-focus structure on the detection surface at the spaced locations.

28. The ultrasonic holographic imaging process as defined in claim 24 wherein the object beam is generated by an ultrasonic object transducer and further comprising the step of sequentially moving the object transducer relative to the system axis to sequentially insonify the object, including the out-of-focus structure, at the plurality of acute incident angles.

29. The ultrasonic holographic imaging process as defined in claim 24 further comprising the steps of (1) generating a sequence of optical images of the selected object in which the out-of-focus structure is located at different locations in the images, (2) converting the optical images to a sequence of digitized electronic images, and (3) averaging the electronic signals of the sequence of digitized electronic images to neutralize those signals corresponding to the out-of-focus structure.

30. The ultrasonic holographic imaging process as defined in claim 24 further comprising the steps (1) generating a sequence of optical images of the selected object in which the out-of-focus structure is located at different locations in the images, and (2) averaging the sequence of images to neutralize the out-of-focus structure relative to the structure in the selected plane.

* * * * *